US009572631B2

(12) United States Patent
Gogarnoiu

(10) Patent No.: US 9,572,631 B2
(45) Date of Patent: Feb. 21, 2017

(54) ASYMMETRICAL DENTAL TOOL WITH COOLING CHANNELS

(71) Applicant: Form and Function Dental Services, P.C., Wynnewood, PA (US)

(72) Inventor: Dumitru Gogarnoiu, Wynnewood, PA (US)

(73) Assignee: FORM AND FUNCTION DENTAL SERVICES, P.C., Wynnewood, PA (US)

( * ) Notice: Subject to any disclaimer, the term of this patent is extended or adjusted under 35 U.S.C. 154(b) by 44 days.

(21) Appl. No.: 14/197,886

(22) Filed: Mar. 5, 2014

(65) Prior Publication Data

US 2015/0250556 A1 Sep. 10, 2015

(51) Int. Cl.
| | | |
|---|---|---|
| A61C 1/10 | (2006.01) | |
| A61C 1/00 | (2006.01) | |
| A61C 17/02 | (2006.01) | |
| A61C 8/00 | (2006.01) | |
| A61C 1/07 | (2006.01) | |
| A61C 1/06 | (2006.01) | |
| A61C 1/05 | (2006.01) | |
| A61C 3/03 | (2006.01) | |

(52) U.S. Cl.
CPC .............. *A61C 1/0069* (2013.01); *A61C 1/05* (2013.01); *A61C 1/06* (2013.01); *A61C 1/07* (2013.01); *A61C 3/03* (2013.01); *A61C 8/0019* (2013.01); *A61C 8/0089* (2013.01); *A61C 17/0202* (2013.01)

(58) Field of Classification Search
CPC ....... A61C 8/0089; A61C 1/00; A61C 1/0061; A61C 1/0069; A61C 1/02; A61C 1/07

USPC ..................... 433/82, 84, 165–166
See application file for complete search history.

(56) References Cited

U.S. PATENT DOCUMENTS

| | | | | |
|---|---|---|---|---|
| 3,842,632 A | * | 10/1974 | Nelson ..................... | B21K 5/02 433/165 |
| 4,021,920 A | * | 5/1977 | Kirschner .......... | A61B 17/1644 433/165 |
| 4,185,383 A | * | 1/1980 | Heimke ................... | A61C 8/00 433/173 |
| 4,279,598 A | * | 7/1981 | Scheicher .......... | A61B 17/1673 433/173 |
| 5,205,817 A | * | 4/1993 | Idemoto ......... | A61B 17/320068 604/22 |

(Continued)

FOREIGN PATENT DOCUMENTS

| | | |
|---|---|---|
| EP | 2 422 737 A1 | 2/2012 |
| WO | WO 98/31295 | 7/1998 |
| WO | WO 2005/079696 A1 | 9/2005 |

OTHER PUBLICATIONS

International Search Report and Written Opinion issued in PCT/US2014/056236 mailed Nov. 25, 2014.

*Primary Examiner* — Matthew Nelson
(74) *Attorney, Agent, or Firm* — RatnerPrestia

(57) ABSTRACT

A device for forming a cavity in a bone includes a body defining a longitudinal axis, a flange defined on the body having two surfaces that meet an edge that is oriented oblique to the longitudinal axis, serrations defined on an outer surface of the body for forming the cavity, an internal fluid passageway defined within the body for directing fluid to the serrations, and a connector extending from the flange that is configured to be connected to an oscillating dental instrument.

17 Claims, 7 Drawing Sheets

(56) References Cited

U.S. PATENT DOCUMENTS

| | | | | |
|---|---|---|---|---|
| 5,636,989 A | * | 6/1997 | Somborac | A61C 8/0018 433/173 |
| 5,816,803 A | * | 10/1998 | Nakanishi | A61C 1/055 433/115 |
| 5,971,758 A | | 10/1999 | Hugo et al. | |
| 6,039,568 A | * | 3/2000 | Hinds | A61C 8/0036 433/173 |
| 6,641,395 B2 | * | 11/2003 | Kumar | A61C 8/0089 433/165 |
| 7,618,258 B2 | | 11/2009 | Gogarnoiu | |
| 7,758,344 B2 | * | 7/2010 | Gogarnoiu | A61C 3/03 433/166 |
| 8,496,478 B2 | * | 7/2013 | Ten Bruggenkate | A61B 17/8625 433/174 |
| 8,998,611 B2 | * | 4/2015 | Yazigi | A61C 1/084 433/165 |
| 2004/0185420 A1 | * | 9/2004 | Schulter | A61C 8/0018 433/173 |
| 2006/0032676 A1 | * | 2/2006 | Papousek | E21B 10/36 175/415 |
| 2007/0148622 A1 | | 6/2007 | Gogarnoiu | |
| 2009/0305189 A1 | * | 12/2009 | Scortecci | A61C 8/0089 433/165 |
| 2010/0167235 A1 | * | 7/2010 | Vercellotti | A61B 17/1615 433/86 |
| 2010/0240009 A1 | * | 9/2010 | Gogarnoiu | A61C 3/03 433/173 |
| 2011/0229845 A1 | * | 9/2011 | Chen | A61C 8/0089 433/86 |
| 2013/0244202 A1 | * | 9/2013 | Chen | A61C 8/0089 433/165 |

\* cited by examiner

ASYMMETRICAL DENTAL TOOL WITH COOLING CHANNELS

FIELD OF THE INVENTION

The invention is related to a dental tool for forming a cavity in bone.

BACKGROUND OF THE INVENTION

Dental implants are used to anchor a mechanical fixture, such as a dental prosthesis, into living bone. The implant is embedded into the bone to provide a solid foundation for connecting the dental prosthesis. The implants and their respective dental prostheses serve numerous purposes, such as to assist the user with chewing, to provide a mating surface for an opposing tooth to prevent the loss of the opposing tooth, and to present an aesthetically pleasing appearance. Prior to inserting the implant into the bone, a cavity is formed in the bone to provide a recess for the insert to be implanted. Forming a cavity in bone to accommodate the implant can generate significant heat and friction, which may result in an infection in the bone. It would be beneficial to reduce the heat generated by the cavity forming operation.

SUMMARY OF THE INVENTION

According to one aspect of the invention, a device for forming a cavity in a bone is provided. The device comprises a body having serrations defined on an outer surface thereof for forming the cavity; an internal fluid passageway defined within the body for directing fluid to the serrations; and a connector defined on one end of the body that is configured to be connected to an oscillating dental instrument.

According to another aspect of the invention, a device for forming a cavity in a bone comprises a body defining a longitudinal axis, a flange defined on the body having two surfaces that meet an edge that is oriented oblique to the longitudinal axis, serrations defined on an outer surface of the body, an internal fluid passageway defined within the body for directing fluid to the serrations, and a connector extending from the flange that is configured to be connected to an oscillating dental instrument.

According to still another aspect of the invention, a dental implant kit comprises a device for forming a cavity in a bone and a dental implant that is configured to be inserted into the cavity. The device comprises a body having serrations defined on an outer surface thereof for forming the cavity, an internal fluid passageway defined in the body for directing fluid to the serrations, and a connector defined on one end of a flange on the body that is configured to be connected to an oscillating dental instrument.

BRIEF DESCRIPTION OF THE DRAWINGS

The foregoing summary, as well as the following detailed description of desired embodiments of the invention, will be better understood when read in conjunction with the appended drawings, which are incorporated herein and constitute part of this specification. For the purposes of illustrating the invention, there are shown in the drawings embodiments that are presently desired. It should be understood, however, that the invention is not limited to the precise arrangements and instrumentalities shown. In the drawings, the same reference numerals are employed for designating the same elements throughout the several figures. In the drawings.

DETAILED DESCRIPTION OF THE INVENTION

Certain terminology is used herein for convenience only and is not to be taken as a limitation on the present invention. The terminology includes the words specifically mentioned, derivatives thereof and words of similar import. The term "facial" is defined to mean a direction closer to the lips and cheek of the user. The term "lingual" is defined to mean a direction closer to the tongue of the user. The term "mesial" is defined to mean a direction closer to an imaginary centerline of the mouth of the user. The term "distal" is defined to mean a direction farther from the imaginary centerline of the mouth. The term "occlusal" is defined to mean the top surface, such as the chewing surface, of a tooth. Further, as used herein, the term "configuration" is defined to mean size and/or shape. The following describes desired embodiments of the invention. However, it should be understood based on this disclosure, that the invention is not limited by the desired embodiments of the invention.

Figure 1:
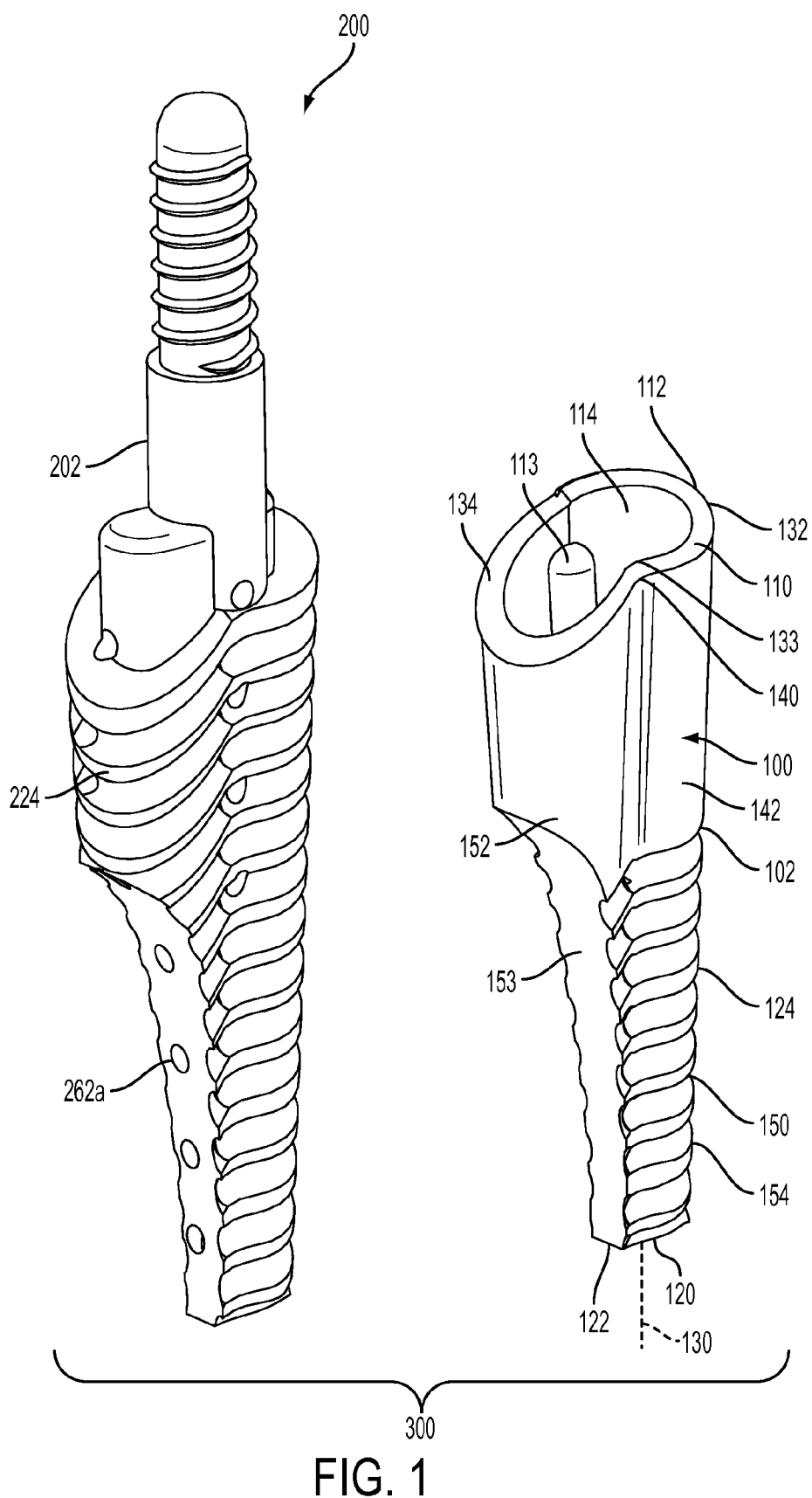
FIG. 1 is a perspective view of a dental implant (see right), as viewed from the top, facial and mesial sides, and a tool (see left) for forming a cavity in bone in which the implant may be inserted.

FIG. 1 depicts a perspective view of a dental implant 100 (see right) and a device or tool 200 (see left) for forming a cavity in tissue and bone (not shown) in which the implant 100 is inserted. One or more dental implants 100 and one or more tools 200 may be provided together as a kit 300, if so desired. One or more prosthetic teeth (not shown) may also be included in the kit. The overall size of the implants 100, tools 200 and teeth may vary to suit the unique facial contours of a patient.

The dental implant 100 includes a unitary body 102 having a first end 110 at its top, a second end 120 at its bottom, and a longitudinal axis 130 extending between the first end 110 and the second end 120. The body 102 has a non-circular cross-section along its length. The first end 110 includes a flange 112. An opening 114 is defined in the flange 112 that extends inward along longitudinal axis 130 toward the second end 120. A post 113 is mounted in the opening 114 of the implant 100 to which a prosthetic tooth (not shown) is coupled.

The flange 112 includes a first surface 132 that is slanted at a first angle $\beta 1$ (see FIG. 7) relative to longitudinal axis 130. Desirably, the first surface 132 extends obliquely relative to the longitudinal axis 130. The first surface 132 forms a slanted mesiodistal face. The flange 112 also includes a second surface 134 that is slanted at a second angle $\beta 2$ (see FIG. 5) relative to the longitudinal axis 130. The second surface 134 forms a slanted facial face. The second surface 134 extends obliquely to longitudinal axis 130 and also at an angle to first surface 132. The second surface 134 may be slanted obliquely relative to the first surface 132, or alternatively, second surface 134 may extend perpendicularly to the first surface 132.

Both the slanted mesiodistal face and the facial face may have angles that vary from shallow to steep, depending on the facial contours of the patient into which the implant 100 is being inserted. Desirably, each angle $\beta 1$, $\beta 2$ extends between about 5 degrees and 45 degrees relative to the longitudinal axis 130, although those skilled in the art will recognize that angles β1, β2 may extend at different angles as well. Further, while the first and second surfaces 132, 134 are depicted in FIG. 1 to extend approximately one half of the flange 112, those skilled in the art will recognize that the first and second surfaces 132, 134 may extend along different distances of the flange 112.

With the first and second surfaces 132, 134 slanting at different angles β1, β2, the flange 112 can be said to have a compound slant relative to longitudinal axis 130. For the implant 100, the compound slant is a mesiodistal slant and a facial slant. A mesiodistal slant and a facial slant will satisfy the clinical requirements of both aesthetics and functionality for the implant 100. These slants allow the implant 100 to obtain perfect or near perfect alignment with the coronal part of the edentulous ridge of bone after insertion.

Figure 4:
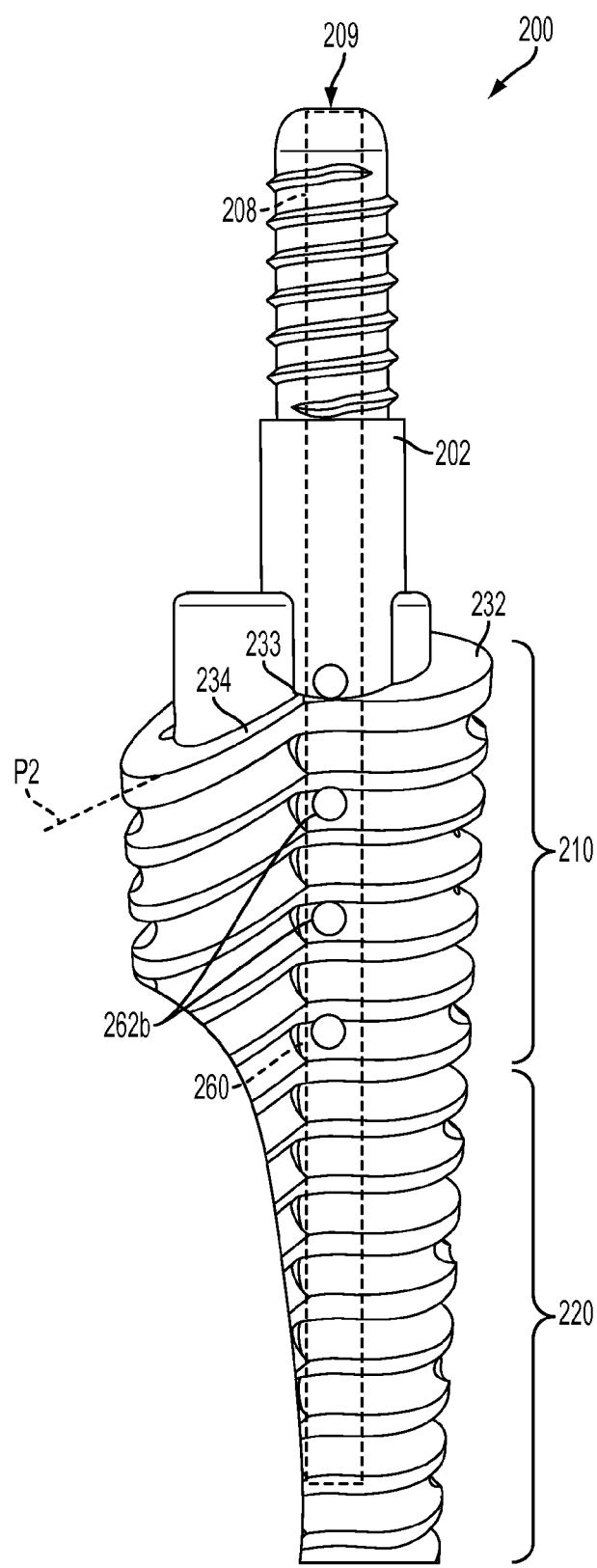
FIG. 4 is a right side elevation view of the tool of FIG. 1.
Figure 6:
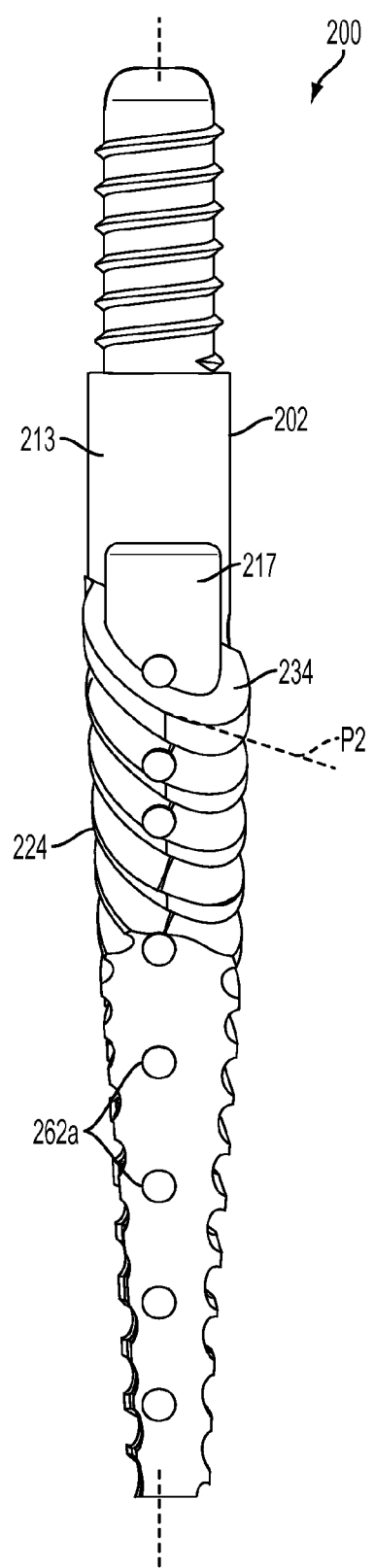
FIG. 6 is a front elevation view of the tool of FIG. 1.
Figure 7:
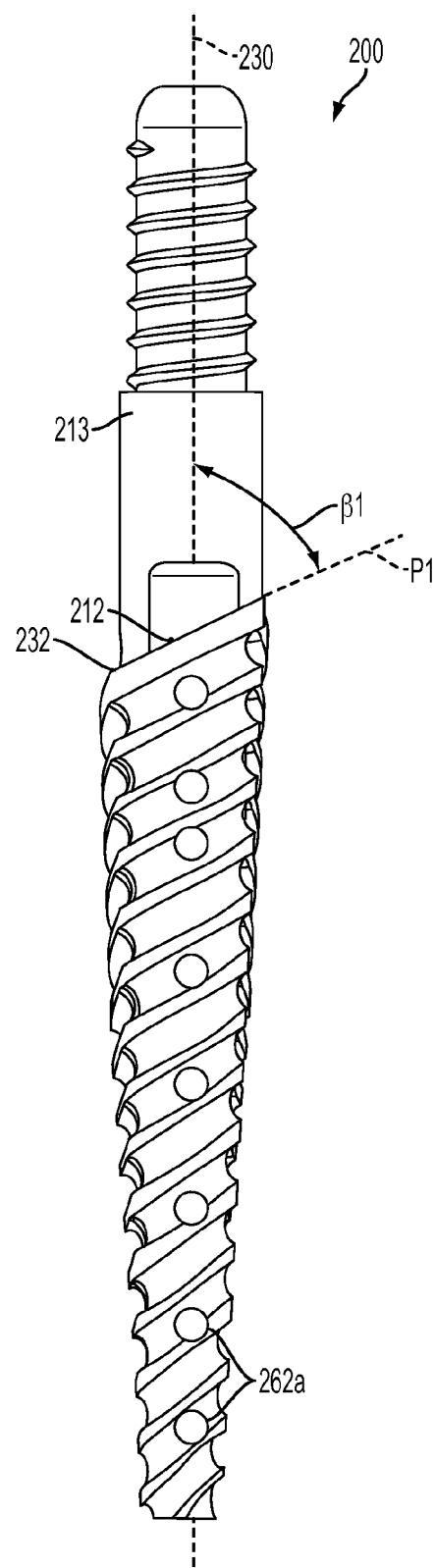
FIG. 7 is a rear elevation view of the tool of FIG. 1.

The flange 112 is formed by a first plane P1 (see the flange 212 of FIG. 7 having the same plane P1) that extends along first surface 132 and out of the plane of FIG. 1 obliquely to longitudinal axis 130 along both a mesiodistal plane and also in a facial plane, and also a second plane P2 (see the flange 212 of FIG. 5 having the same plane P2) that extends along second surface 134 and out of the plane of FIG. 4 obliquely to longitudinal axis 130 along both the mesiodistal plane and also in a lingual plane. Stated differently, both surfaces 132 and 134 of the flange 112 extend obliquely (i.e., neither parallel nor perpendicular) with respect to a horizontal plane and a vertical plane of a Cartesian coordinate system. As can be seen in FIGS. 6 and 7, both planes P1, P2 extend obliquely relative to longitudinal axis 130. An intersection of planes P1 and P2 form an edge 133 that extends oblique to longitudinal axis 130.

The body 102 desirably includes a highly polished collar 140 that extends approximately 0.5 mm, for example, from the first end 110 toward the second end 120. The polished collar 140 allows the development of natural gingival sulcus around the implant 100. A rough surface 142 desirably extends approximately 1.5 mm below collar 140 toward second end 120. The rough surface 142 accommodates biologic width of connective tissue that typically surrounds a living tooth and provides a surface for connective tissue to attach after implant 100 is inserted into the bone.

The second end 120 of the body 102 forms a tapered root 150 that extends away from first end 110. The second end 120, as well as root 150, extends asymmetrically about longitudinal axis 130. The root 150 includes a root portion 152 that extends from the first end 110 and an extension portion 154 that extends from the root portion 152, away from the first end 110, and primarily along one side of the longitudinal axis 130.

The root 150 has a generally concave face 153 at an interface between the root portion 152 and the extension portion 154. The root 150 tapers from larger to smaller in a direction away from the first end 110. The asymmetrical aspect of root 150 with respect to the longitudinal axis 130 prevents rotation of the implant 100 within the body cavity after insertion of the implant 100 into the body cavity. The concave face 153 of the root 150 generally mimics a tooth root and provides for a relatively comparable fit of the root 150 within the body cavity. The second end 120 is closed with a tip 122. The second end 120 also includes external ridges or serrations 124 that are used to secure the implant 100 into a bone. The serrations 124 may be mechanical threads, if so desired.

Further details of the implant are described in U.S. Pat. No. 7,758,344 to Gogarnoiu (referred to as the '344 patent), which is incorporated by reference herein in its entirety and for all purposes.

FIGS. 2-7 depict the tissue and bone cutting tool 200 for forming a cavity in a bone in which the implant 100 is inserted. The tool 200 is uniquely configured to form a hole in bone and/or tissue. As evidenced by FIG. 1, the tool 200 shares much of the same geometry as the implant 100.

More particularly, the tool 200 includes a body 202 having a first end 210, a second end 220, and a longitudinal axis 230 extending between first end 210 and the second end 220. The body 202 has a non-circular cross-section along its entire length. A circumference of the body 202 is also non-constant along its length dimension.

The first end 210 of the body 202 includes a flange 212. The geometries of the flanges 112 and 212 are substantially identical. Like the flange 112 of the implant 100, the flange 212 of the tool 200 extends asymmetrically about the longitudinal axis 230. As shown in FIG. 7, the flange 212 of the tool 200 includes a first surface 232 that is slanted at a first angle β1 relative to longitudinal axis 230. Desirably, the first surface 232 extends obliquely relative to the longitudinal axis 230. The first surface 232 forms a slanted mesiodistal face.

Figure 5:
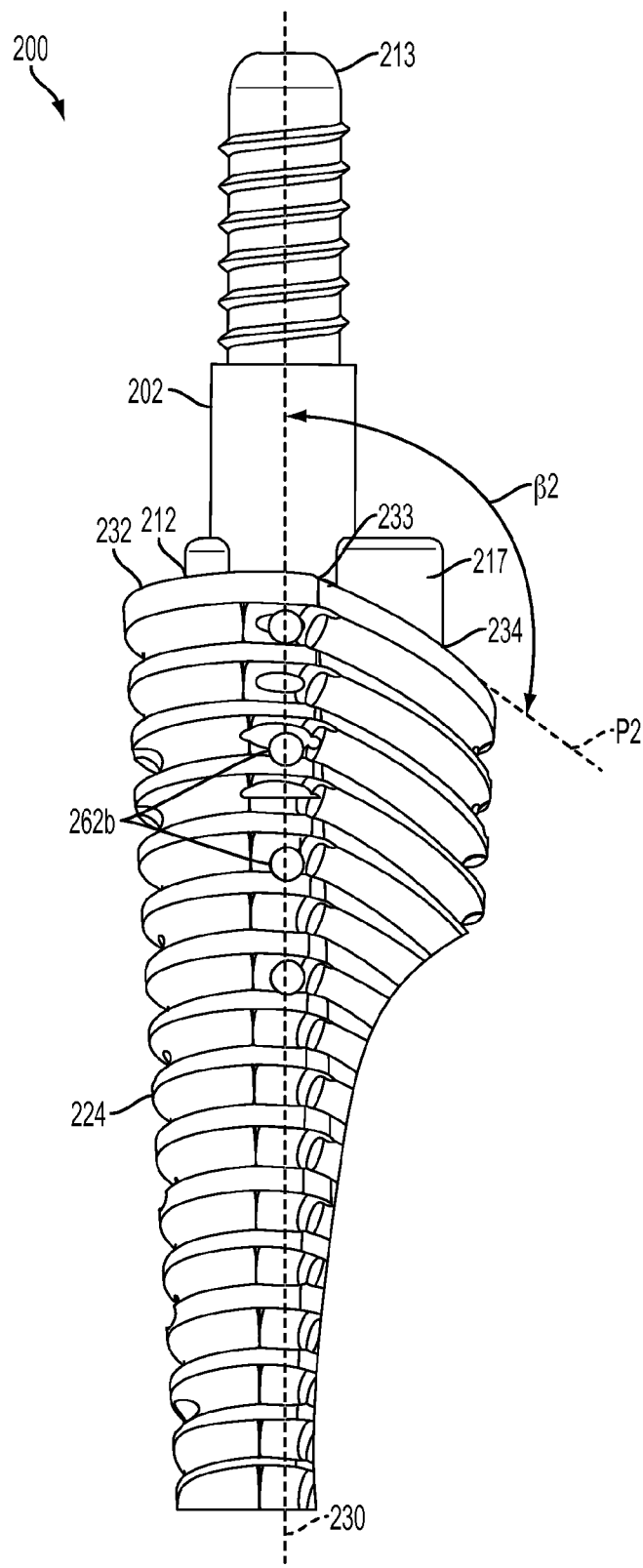
FIG. 5 is a left side elevation view of the tool of FIG. 1.

As shown in FIG. 5, the flange 212 also includes a second surface 234 that is slanted at a second angle β2 relative to the longitudinal axis 230. The second surface 234 forms a slanted facial face. The second surface 234 extends obliquely to longitudinal axis 230 and also at an angle to the first surface 232. The second surface 234 may be slanted obliquely relative to first surface 232, or alternatively, the second surface 234 may extend perpendicularly to the first surface 232.

Figure 2:
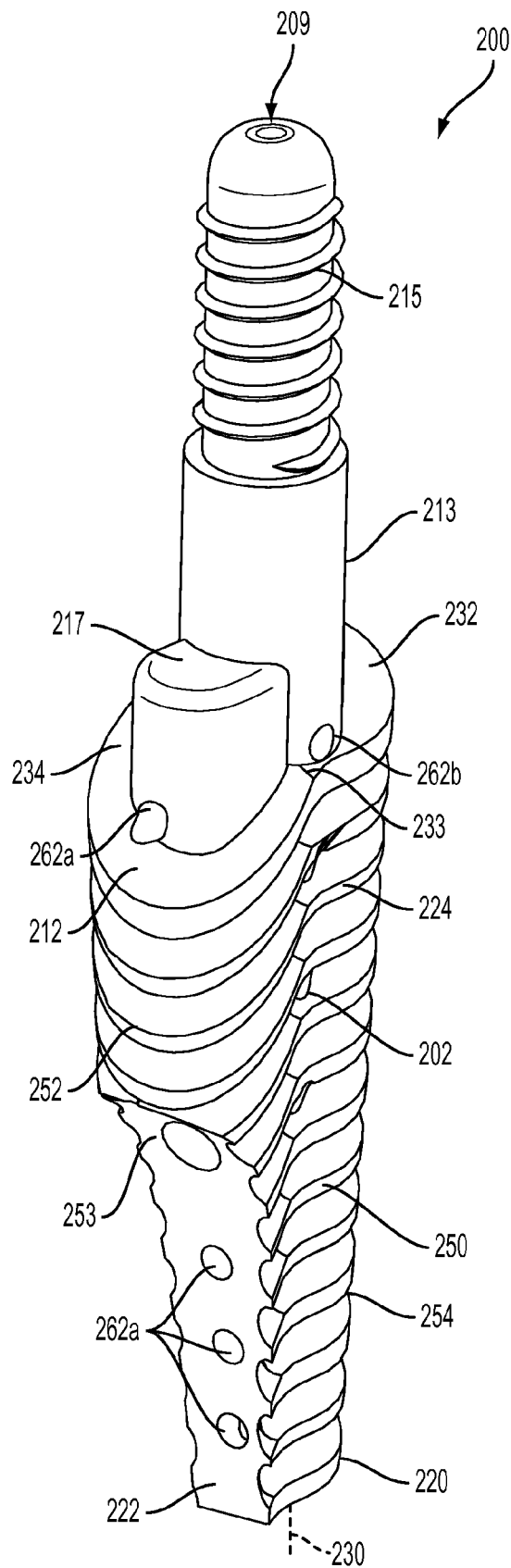
FIGS. 2 and 3 are perspective views of the tool of FIG. 1.
Figure 3:
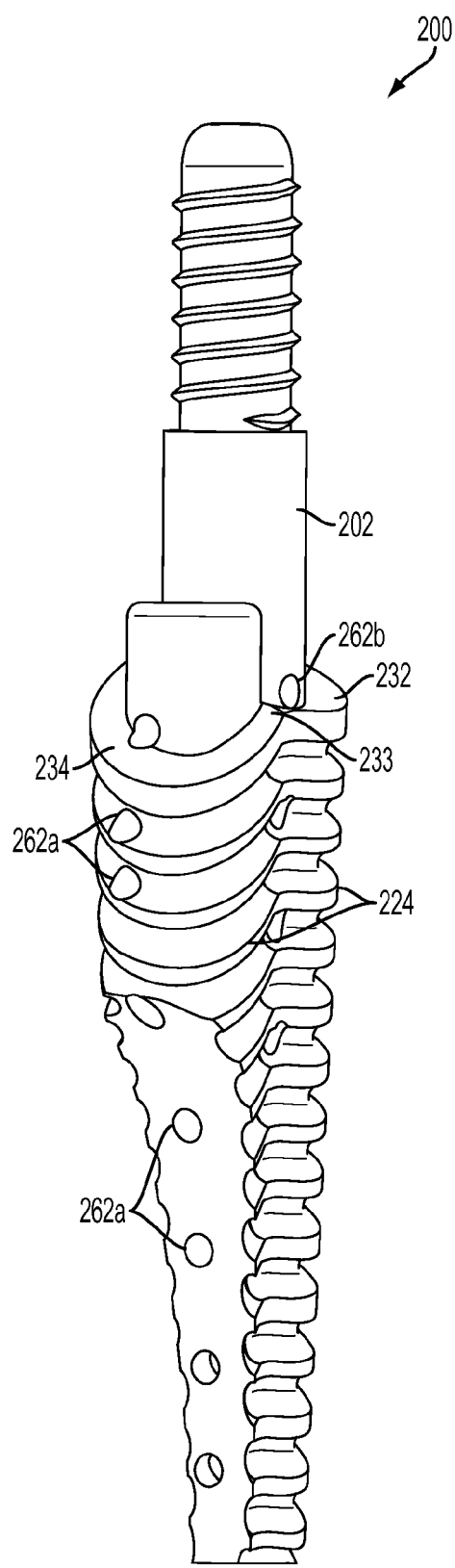

Like the implant 100, both the slanted mesiodistal face and the facial face of the tool 200 may have angles that vary from shallow to steep, depending on the facial contours of the patient. Desirably, each angle β1, β2 extends between about 5 degrees and 45 degrees relative to the longitudinal axis 230, although those skilled in the art will recognize that angles β1, β2 may extend at different angles as well. Further, while the first and second surfaces 232, 234 are depicted in FIG. 2 to extend approximately one half of flange 212, those skilled in the art will recognize that the first and second surfaces 232, 234 may extend along different distances of the flange 212.

With the first and second surfaces 232, 234 slanting at different angles β1, β2, the flange 212 can be said to have a compound slant relative to longitudinal axis 230. For the tool 200, the compound slant is a mesiodistal slant and a facial slant. Only a mesiodistal slant and a facial slant will satisfy the clinical requirements of both aesthetics and functionality for the implant 100. The slants of the tool 200, which form a recess to accommodate the implant 100, obtain perfect or near perfect alignment with the coronal part of the edentulous ridge of bone after insertion.

The flange 212 is formed by a first plane P1 that extends along first surface 232 and out of the plane of FIG. 7 obliquely to longitudinal axis 230 along both a mesiodistal plane and also in a facial plane. A second plane P2 extends along the second surface 234 and out of the plane of FIG. 4 obliquely to longitudinal axis 230 along both the mesiodistal plane and also in a lingual plane. Stated differently, both surfaces 232 and 234 of the flange 212 extend obliquely (i.e., neither parallel nor perpendicular) with respect to a horizontal plane and a vertical plane of a Cartesian coordinate system. As can be seen from FIGS. 6 and 7, both planes P1, P2 extend obliquely relative to longitudinal axis 230. An intersection of planes P1 and P2 form an edge 233 that extends oblique to longitudinal axis 230.

The second end 220 of the body 102 is generally tapered from smaller to larger in a direction toward the first end 210. The second end 220 forms a tapered root 250 that extends away from the first end 210. The second end 220, as well as the root 250, extends asymmetrically about the longitudinal axis 230. Root 250 includes a root portion 252 that extends from the first end 210 and an extension portion 254 that extends from the root portion 252, away from the first end 210, and primarily along one side of the longitudinal axis 230. The second end 220 is closed with a tip 222.

The root 250 has a generally concave face 253 at an interface between the root portion 252 and the extension portion 254. The root 250 tapers from larger to smaller in a direction away from first end 210. The asymmetrical aspect of root 250 with respect to the longitudinal axis 230 forms a cavity in the bone that prevents rotation of the implant 100 within the bone cavity after insertion of the implant 100 into the bone cavity. The concave face 253 of the root 250 generally mimics a tooth root and provides for a relatively comparable fit of the root 250 within the bone cavity.

Serrations 224 (i.e., sharp edges) are defined on the outer surface of the tool body 202 beneath the flange 212. The serrations 224 are configured to cut away tissue and bone when the tool 200 is affixed to an oscillating dental instrument. The serrations 224 are omitted from the convex face 253. The serrations 224 may be replaced with mechanical threads, if so desired.

A circular post 213 extends upward from the flange 212 to which an oscillating dental instrument (not shown) is releasably coupled. The post 213 includes threads 215 for attachment to the oscillating dental instrument, although other means for attachment are envisioned. The threaded post 213 is positioned substantially on the first surface 232 of the flange 212. The threaded post 213 may also be referred to herein as a connector. A semi-circular post 217 adjoins the base of the circular post 213. The semi-circular post 217 is enhances the structural integrity of the tool 200.

The oscillating dental instrument may be electronic and/or pneumatic; it may vibrate at either sonic or ultrasonic frequencies; and it may incorporate either a magnetostrictive or piezoelectric element. The oscillating dental instrument may be, for example, a SONICflex 2003L scaling instrument, which is distributed by Kayo, Inc. The SONICflex 2003L scaling instrument includes a threaded connector to which the threads 215 of the tool 200 may be releasably attached.

Referring now to FIG. 4, an internal fluid passageway 208 is defined along the length dimension of the tool 200. The passageway 208 includes a vertically-oriented blind hole 260 (shown in broken lines in FIG. 4) that extends along a substantial portion of the longitudinal axis 230 of the tool 200. The hole 260 intersects and is fluidly connected to a plurality of horizontally-oriented holes 262a and 262b (referred to collectively as holes 262). The axis of each hole 262 is substantially perpendicular to the longitudinal axis 230 of the body 202. The holes 260 and 262 together form an interconnected network of fluid passages.

The holes 262a are defined on the front and rear sides of the body 202, whereas the holes 262b are defined on the right and left sides of the body 202. Stated differently, the holes 262a and 262b are rotated by 90 degrees with respect to each other. Many of the holes 262 are thru-holes that pass through the entire thickness of tool body 202, whereas some of the holes 262 may be blind holes. Every hole 262 intersects the vertically-oriented blind hole 260. The holes 262a are staggered along the first and second ends 210 and 220 of the tool body 202, respectively, whereas the holes 262b are only staggered along the first end 210 of the tool body 202. One or more holes 262a may intersect one or more holes 262b.

The internal fluid passageway 208 extends from the opening 209 at the top end of the post 213 to an elevation that is above the closed end 222 of the tool 200. Thus, the passageway 208 does not extend through the closed end 222 of the tool 200. However, it is envisaged that the passageway 208 could extend through the end 222 of the tool 200, if so desired.

In use, cooling fluid is delivered from the oscillating dental instrument into the opening 209 of the internal fluid passageway 208 of the tool 200. The cooling fluid initially travels downward through the blind hole 260 and is expelled through the side holes 262 of the internal fluid passageway 208 in an effort to reduce the heat generated at the interface between the serrations 224 and the bone. Cooling the bone is beneficial to avoid exposing the bone to excessive heat, which could cause infection at the bone site. The cooling fluid that is used may be air or water, for example, or any other cooling fluid.

The entire tool 200 may be formed from a 3-D printing process. According to one exemplary method of forming the tool 200 using the 3-D printing process, a 3-D printer applies a thin layer of a biocompatible material in powder form to a platform and a laser beam fuses together the powder particles of the thin layer. This process is repeated layer by layer until the tool 200 (including the holes 260 and 262) is completely formed. Alternatively, the tool 200 may be formed by a casting process or a machining process. The tool 200 may be composed of a biocompatible material, such as Titanium, Zirconium or a blend of different materials.

Although the invention is illustrated and described herein with reference to specific embodiments, the invention is not intended to be limited to the details shown. Rather, various modifications may be made in the details within the scope and range of equivalents of the claims and without departing from the invention.

What is claimed:
1. A device for forming a cavity in a bone for use with an oscillating dental instrument comprising:
   a body defining a longitudinal axis;
   a flange defined on the body having two surfaces that meet an edge, which is oriented oblique to the longitudinal axis;
   serrations for forming the cavity that are defined on an outer surface of the body at an elevation below the flange, wherein a radial edge of the flange constitutes a top-most serration along the longitudinal axis, and the radial edge of the flange extends around an entire perimeter of the body, and wherein the serrations positioned beneath one surface of the two surfaces of the flange extend non-parallel to the serrations positioned beneath the other surface of the two surfaces of the flange;
   an internal fluid passageway defined in the body for directing fluid to the serrations on the outer surface of the body;
   a plurality of side holes defined on the outer surface of the body that are each connected to the internal fluid passageway for delivering fluid to the serrations on the outer surface of the body, wherein one or more side holes of the plurality of side holes are defined at an elevation above the flange and one or more side holes of the plurality of side holes are defined at an elevation below the flange;

a concave surface formed on the body that is devoid of serrations, wherein the internal fluid passageway passes through said concave surface; and a connector extending from the flange that is configured to be connected to the oscillating dental instrument, the internal fluid passageway extending up the longitudinal axis and through the connector to define an inlet port at a top end of the connector, wherein fluid introduced through the inlet port is distributed through each side hole of the plurality of side holes.

2. The device of claim 1, wherein the internal fluid passageway includes a vertical hole that extends along the longitudinal axis of the body.

3. The device of claim 2, wherein the vertical hole is blind.

4. The device of claim 2, wherein the vertical hole intersects the plurality of side holes that extend to the serrations on the body.

5. The device of claim 4, wherein the plurality of side holes are substantially perpendicular to the vertical hole.

6. The device of claim 4 wherein at least two of the side holes are radially spaced apart with respect to each other about the longitudinal axis of the body.

7. The device according to claim 1, wherein a circumference of the body is non-constant as measured along a length dimension of the body.

8. The device according to claim 1, wherein the flange extends asymmetrically about the longitudinal axis.

9. The device according to claim 1, wherein the two surfaces of the flange are oblique to one another.

10. The device according to claim 1, wherein each surface of the flange is oblique to a vertical Cartesian plane and a horizontal Cartesian plane.

11. The device of claim 1, wherein a cross-section of the body taken along the longitudinal axis is non-circular.

12. A device for forming a cavity in a bone oscillating dental instrument comprising:

a body defining a longitudinal axis and having serrations defined on an outer surface thereof for forming the cavity, a flange defined on the body and having two surfaces that intersect each other, wherein a radial edge of the flange constitutes a top-most serration along the longitudinal axis, and the radial edge of the flange extends around an entire perimeter of the body, and wherein the serrations positioned beneath one surface of the two surfaces of the flange extend non-parallel to the serrations positioned beneath the other surface of the two surfaces of the flange;

an internal fluid passageway defined within the body for directing fluid to the serrations;

a concave surface formed on the body that is devoid of serrations, wherein the internal fluid passageway passes through said concave surface; and a connector defined on one end of a flange of the body that is configured to be connected to the oscillating dental instrument, the internal fluid passageway extending up the longitudinal axis and through the connector to define an inlet port at a top end of the connector;

a plurality of side holes defined on the outer surface of the body that are each connected to the internal fluid passageway for delivering fluid to the serrations on the outer surface of the body, wherein one or more side holes of the plurality of side holes are defined at an elevation above the flange and one or more side holes of the plurality of side holes are defined at an elevation below the flange and each side hole receives fluid distributed through the inlet port on the connector.

13. The device of claim 12, wherein the internal fluid passageway includes a vertical hole that connects to the side holes that extend to the serrations on the outer surface of the body.

14. A dental implant kit comprising:

a device for forming a cavity in a bone including a body defining a longitudinal axis and having serrations for forming the cavity that are defined on an outer surface of the body at an elevation below a flange of the body, the flange having two surfaces that intersect each other, wherein a radial edge of the flange constitutes a top-most serration along the longitudinal axis, and the radial edge of the flange extends around an entire perimeter of the body, and wherein the serrations positioned beneath one surface of the two surfaces of the flange extend non-parallel to the serrations positioned beneath the other surface of the two surfaces of the flange, an internal fluid passageway defined within the body for directing fluid to the serrations, a concave surface formed on the body that is devoid of serrations, wherein the internal fluid passageway passes through said concave surface, a connector defined on one end of the flange of the body that is configured to be connected to an oscillating dental instrument, the internal fluid passageway extending up the longitudinal axis and through the connector to define an inlet port at a top end of the connector, and a plurality of side holes defined on the outer surface of the body that are each connected to the internal fluid passageway for delivering fluid to the serrations on the outer surface of the body, wherein one or more side holes of the plurality of side holes are defined at an elevation above the flange and one or more side holes of the plurality of side holes are defined at an elevation below the flange and each side hole receives fluid distributed through the inlet port on the connector; and a dental implant that is configured to be inserted into the cavity formed by the device.

15. The dental implant kit of claim 14, wherein the two surfaces of the flange meet at an edge that is oriented oblique to the longitudinal axis of the body.

16. The dental implant kit of claim 15 further comprising a flange on the dental implant having two surfaces that meet an edge, which is oriented oblique to a longitudinal axis of the implant.

17. The dental implant kit of claim 16, wherein an angle defined between the edge of the implant and the longitudinal axis of the implant is the same as an angle defined between the edge of the device and the longitudinal axis of the device.

* * * * *